US00PP19918P2

(12) United States Plant Patent
Bradford

(10) Patent No.: US PP19,918 P2
(45) Date of Patent: Apr. 14, 2009

(54) NECTARINE TREE NAMED 'SUGARRED III'

(50) Latin Name: *Prunus persica*
Varietal Denomination: Sugarred III

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 12/003,397

(22) Filed: Dec. 26, 2007

(51) Int. Cl.
*A01H 5/00* (2006.01)

(52) U.S. Cl. ..... Plt./187
(58) Field of Classification Search ..... Plt./187
See application file for complete search history.

(56) References Cited

U.S. PATENT DOCUMENTS

PP7,507 P 4/1991 Bradford

*Primary Examiner*—Annette H Para
*Assistant Examiner*—June Hwu

(57) ABSTRACT

The present invention relates to a new and distinct variety of nectarine tree, *Prunus persica,* broadly characterized by a medium size, vigorous, hardy, self-fertile, productive and regular bearing tree. The variety blooms during the mid season and requires about 600 chilling hours. The fruit matures under the ecological conditions described in early July, with first picking Jul. 6, 2007. The fruit is uniformly large in size, acidic and sweet in flavor, globose in shape, clingstone in type, firm and melting in texture, mostly red in skin color, and nearly full red in flesh color.

1 Drawing Sheet

Botanical classification: *Prunus persica.*
Variety denomination: 'Sugarred III'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'Sugarred III'.

The present variety was hybridized by me in 1992 as a first generation cross using 'Spring Bright' (U.S. Plant Pat. No. 7,507) nectarine as the selected seed parent and an unnamed nectarine (unpatented) as the selected pollen parent. The fruit of this cross was gathered that summer, and the seeds were removed, cracked, stratified, germinated, and grown as seedlings on their own root in my greenhouse. Upon reaching dormancy the seedlings were transplanted as a group to a cultivated area of my experimental orchard located near Le Grand, Calif., in Merced County (San Joaquin Valley). During the fruit evaluation season of 1996 I selected the present variety as a single tree from the group of seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'Spring Bright' nectarine, by producing nectarines that are firm, mostly red in skin color, clingstone in type, and acidic in flavor, but is distinguished therefrom by producing fruit that is nearly full red instead of yellow in flesh color, that is larger in size, and that matures about twenty days later.

The present variety is similar to its pollen parent, an unnamed nectarine, by producing nectarines that are nearly full red in skin color, firm in texture, and acidic in flavor, but is distinguished therefrom by producing fruit that is nearly full red in flesh color instead of yellow, that is larger in size, that has a sweet kernel instead of bitter, and that matures about forty days later.

The present variety is similar to 'Grand Bright' (U.S. Plant Pat. No. 16,494) nectarine by having mostly globose glands instead of reniform and by producing nectarines that are nearly full red in skin color, acidic in flavor, and that mature in mid July, but is distinguished therefrom by producing fruit that is nearly full red in flesh color instead of mostly yellow, that is firmer in texture, and that has a longer harvest duration.

SUMMARY OF VARIETY

In summary, the present variety is characterized by a medium size, vigorous, hardy, self-fertile, productive and regular bearing tree. The variety blooms during the mid season and requires about 600 chilling hours. The fruit matures under the ecological conditions described in early July, with first picking on Jul. 6, 2007. The fruit is uniformly large in size, acidic and sweet in flavor, globose in shape, clingstone in type, firm and melting in texture, mostly red in skin color, and nearly full red in flesh color.

DRAWING

The accompanying photograph consists of five whole fruits positioned to display the characteristics of the skin color and form, one sliced fruit to reveal the flesh and stone, two insets to reveal buds and a blossom, characteristic leaves, and a typical stone.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jul. 6, 2007, on the original tree during its fifteenth growing season. The blossom and flower descriptions were made the previous blooming season. All major color code designations are by reference to the Inter-Society Color Council, National Bureau of Standards. Common color names are also used occasionally.

Parentage

Seed parent: 'Spring Bright' (U.S. Plant Pat. No. 7,507) nectarine.

Pollen parent: Unnamed nectarine.

Tree

Size: Medium, reaching and maintaining a height of 12' [3.66 m.] and a spread of 10' [3.05 m.] after fifteen growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning necessary.

Fertility: Self-fertile.

Bearing: Regular bearer with no alternate bearing yet observed.

Approximate chilling requirement: 600 hours.

Trunk:

*Size.*—Medium, reaching a maximum diameter of 6" [152 mm.] after the fifteenth growing season.

*Texture.*—Shaggy.

*Bark color.*—A Dark yellowish brown [78. d.yBr] and Moderate yellowish brown [77. m.yBr] variegation with Dark orange yellow [72. d.OY] crevices present.

*Lenticels.*—Approximate Number Per Square Inch: 5. Color: Dark orange yellow [72. d.OY]. Average Size: ½" [12.7 mm.]. Shape: Eye-shaped, elongated.

Branches:

*Size.*—Diameter of limb is 3¾" [95.3 mm.] measured 12" above the crotch, 2¼" [57.2 mm.] measured 12" above the first fork.

*Texture.*—Smooth on first and second year wood, increasing roughness with age.

*Color.*—1st Year Wood Topside: Grayish red [19. gy.R]. 1st Year Wood Underside: Brilliant yellow green [116. brill.YG]. Older Wood: Strong yellowish brown [74. s.yBr].

*Lenticels.*—Number Per Square Inch: More than 60 on second year wood. Color: Moderate orange yellow [71. m.OY]. Average size: 1/32" [0.8 mm.] on second year wood. Shape: Rectangular, elongated.

Leaves:

*Size.*—Medium. Average Length: 5½" [140 mm.]. Average Width: 1½" [38 mm.].

*Arrangement.*—Alternate.

*Thickness.*—Medium.

*Form.*—Elliptical.

*Apex.*—Acuminate.

*Base.*—Acute to rounded, with an average base angle of 80 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: ½" [12.7 mm.]. Average Thickness: 1/16" [1.6 mm.]. Color: Brilliant yellow green [116. brill.YG].

*Stipules.*—Number: Usually 2 per leaf, up to 6 per growing tip. Average Length: ⅜" [9.5 mm.]. Color: Very yellow green [115. v.YG] becoming Moderate reddish brown [43. m.rBr] with maturity.

*Glands.*—Number: 2 to 4 per leaf. Position: Mostly alternate with some opposite, positioned on petiole and base of blade. Size: Medium. Form: Mostly globose with a few small reniform. Color: Brilliant yellow green [116. brill.YG] becoming Dark yellowish brown [78. d.yBr] with age.

*Leaf buds.*—Pointed, medium in size.

Flower buds:

*Hardiness.*—Hardy, with respect to central California winters.

*Diameter.*—Typically ⅜" [9.5 mm.] 1 week before bloom.

*Length.*—Typically 9/16" [14.3 mm.] 1 week before bloom.

*Form.*—Not appressed.

*Surface.*—Pubescent.

*Tip color.*—Dark purplish pink [251. d.pPk].

Flowers: Perfect, complete, perigynous, usually a single pistil, typically thirty or more stamens, five sepal and petal locations alternately positioned.

*Type.*—Showy, large.

*Average flower diameter.*—2" [50.8 mm.].

*Number of petals.*—Usually five, occasional extra petal fragments, double blossoms rarely observed.

*Petal shape.*—Circular to oval.

*Petal margin.*—Entire, slightly wavy, occasional notches.

*Average petal diameter.*—13/16" [20.6 mm.].

*Average petal length.*—⅞" [22.2 mm.].

*Petal apex.*—Rounded.

*Petal base.*—Rounded to somewhat truncate.

*Petal color.*—Pale pink [7. p.Pk] toward the apex, Dark purplish pink [251. d.pPk] toward the base on both sides.

*Anther color.*—Moderate red [15. m.R] over a Light yellow [86. l.Y] center at bloom onset.

*Stigma color.*—Pale yellow green [121. p.YG].

*Sepal color.*—Dark purplish red [259. d.pR] on the outer surface.

*Sepal length.*—15/64" [6 mm.].

*Sepal width.*—3/16" [5 mm.].

*Sepal apex.*—Rounded to elliptical to match the sepal length and width.

*Sepal margin.*—Fairly smooth.
*Average pistil length.*—11/16" [17.5 mm.].
*Average stamen length.*—9/16" [14.3 mm.].
*Fragrance.*—Moderate.
*Blooming period.*—Medium, two days after 'Spring Bright' (U.S. Plant Pat. No. 7,507) nectarine.
*Onset of bloom.*—One percent on Mar. 4, 2007.
*Date of full bloom.*—Mar. 11, 2007.
*Duration of bloom.*—One to two weeks, dependent on ambient temperature.
*Number per cluster.*—1 to 3 with single flowers most common.

FRUIT

Maturity when described: Firm ripe, Jul. 18, 2007.
Date of first picking: Jul. 6, 2007.
Date of last picking: Jul. 20, 2007.
Size: Uniform, large.
*Average diameter axially.*—3" [76 mm.].
*Average diameter across suture plane.*—2⅞" [73 mm.].
*Average diameter across cheek plane.*—2⅞" [73 mm.].
*Typical weight.*—9.1 ounces [258 grams].
Form: Uniform, globose, mostly symmetrical.
*Longitudinal section form.*—Slightly oblong.
*Axial view.*—Round.
Suture: A sharp groove inside the stem cavity, a shallow trough along the side, and a shallow groove toward the apex, ending beyond the pistil point.
Ventral surface: Rounded, lipped stronger toward the apex.
Lips: Mostly equal.
Cavity: Flaring, elongated in the suture plane, suture showing on one side, Moderate orange yellow [71. m.OY] stem markings present.
*Depth.*—¾" [19.1 mm.].
*Breadth.*—1⅛" [28.6 mm.].
Base: Rounded to slightly truncate.
Apex: Rounded, but slightly cordate if viewed parallel to the suture.
Pistil point: Both apical and oblique, negligible in length, mostly depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Astringent.
*Tendency to crack.*—None observed in dry season.
*Color.*—Very deep red [14. v.deep R] smoothly blending into a Moderate reddish orange [37. m.rO] background with very little Light orange yellow [70. l.OY] freckling toward the apex.
Flesh:
*Color.*—Dark red [16. d.R] streaking over a Moderate orange [53. m.O] background.
*Surface of pit cavity.*—Covered with Very dark red [17. v.d.R] broken fibers when twisted from stone.
*Amygdalin.*—Abundant.
*Juice.*—Abundant, rich.
*Texture.*—Firm, crisp.
*Fibers.*—Abundant, tough.
*Ripens.*—Slightly earlier at the apex.
*Flavor.*—Acidic and sweet, typically 15 brix.
*Aromas.*—Slight.
*Eating quality.*—Very good.

STONE

Type: Clingstone.
Form: Oval.
Hilum: Narrow, oblong.
Base: Slightly oblique.
Apex: Acuminate with a 1/16" [1.6 mm.] tip.
Sides: Equal.
Surface: Irregularly furrowed horizontally toward the apex, pitted toward the base.
Ridges: Jagged.
External color: Deep brown [56. deep Br].
Pit wall color when cracked: Strong yellowish brown [74. s.yBr].
Cavity surface color: Strong brown [55. s.Br].
Average pit wall thickness: ¼" [6.4 mm.].
Average width: 1⅛" [28.6 mm.].
Average length: 1½" [38.1 mm.].
Average breadth: 15/16" [23.8 mm.].
Tendency to split: Very slight.
Kernel:
*Form.*—Oval.
*Skin color.*—Brilliant yellow [83. brill.Y] when first removed.
*Pellicle color.*—Dark grayish yellow [91. d.gy.Y].
*Vein color.*—Grayish yellow [90. gy.Y].
*Taste.*—Sweet.
*Viable.*—Yes.
*Average width.*—½" [12.7 mm.].
*Average length.*—13/16" [20.6 mm.].
*Amygdalin.*—Scant.

USE

Market: Fresh market and long distance shipping.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is similar to its seed parent, 'Spring Bright' (U.S. Plant Pat. No. 7,507) nectarine, by producing nectarines that are firm, mostly red in skin color, clingstone in type, and acidic in flavor, but is distinguished therefrom by producing fruit that is nearly full red instead of yellow in flesh color, that is larger in size, and that matures about twenty days later.

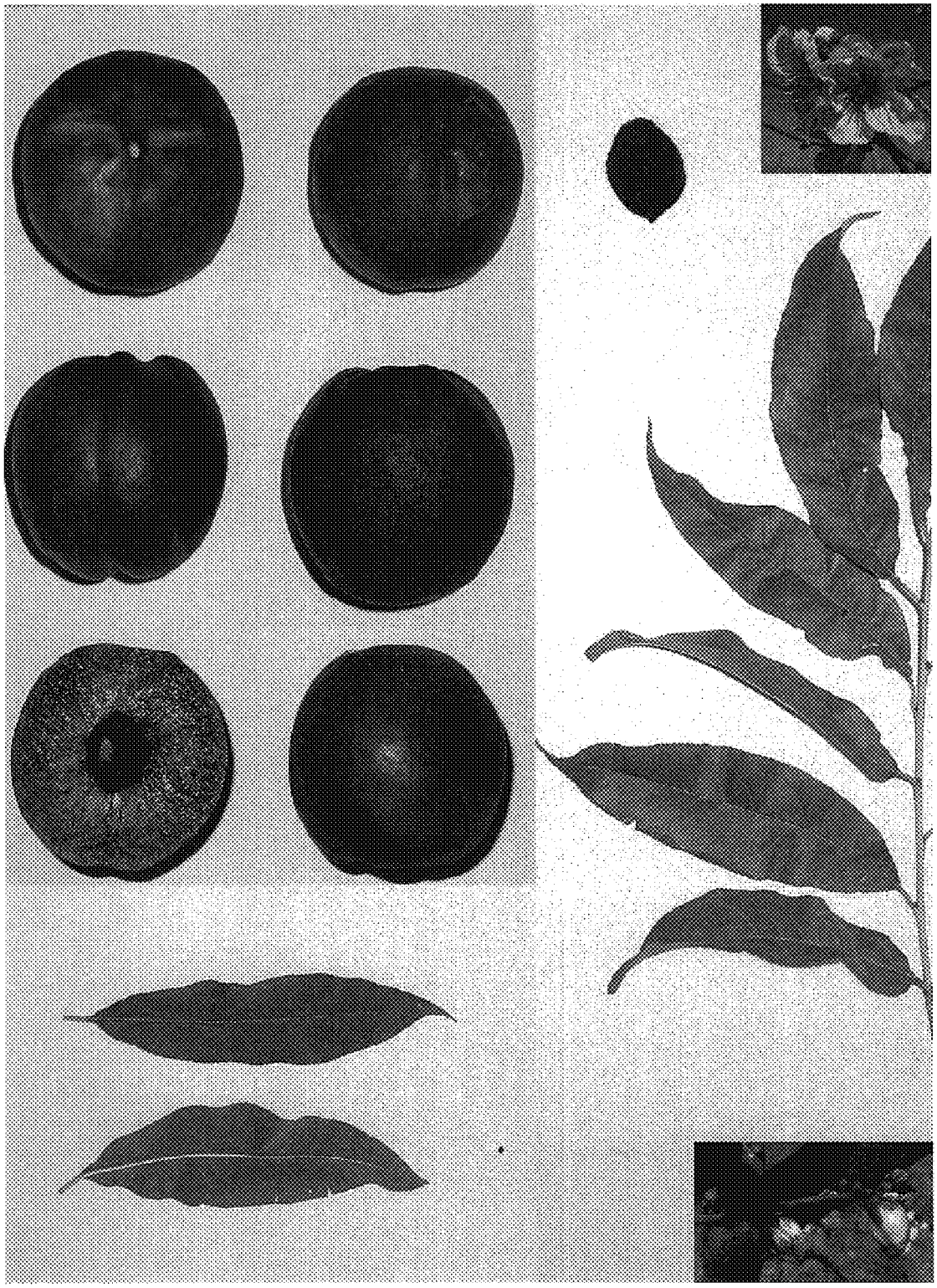

* * * * *